United States Patent

Dutzmann et al.

Patent Number: 5,059,616
Date of Patent: Oct. 22, 1991

[54] FUNGICIDAL COMBINATIONS OF ACTIVE COMPOUNDS

[75] Inventors: Stefan Dutzmann, Duesseldorf; Wilhelm Brandes, Leichlingen; Dieter Berg, Wuppertal; Graham Holmwood, Wuppertal; Detlef Wollweber, Wuppertal, all of Fed. Rep. of Germany

[73] Assignee: Bayer Aktiengesellschaft, Leverkusen, Fed. Rep. of Germany

[21] Appl. No.: 592,158

[22] Filed: Oct. 3, 1990

[30] Foreign Application Priority Data

Oct. 18, 1989 [DE] Fed. Rep. of Germany ....... 3934714

[51] Int. Cl.$^5$ ..................... A01N 43/36; A01N 43/64
[52] U.S. Cl. .................... 514/383; 514/422; 514/427
[58] Field of Search ......... 514/383, 422, 427

[56] References Cited

U.S. PATENT DOCUMENTS 4,723,984 2/1988 Holmwood et al. ............ 71/76
4,914,122 4/1990 Wollweker et al. ............ 514/422

FOREIGN PATENT DOCUMENTS 0052424 5/1982 European Pat. Off. .
3737984 8/1989 Fed. Rep. of Germany .

Primary Examiner—Allen J. Robinson
Attorney, Agent, or Firm—Sprung Horn Kramer & Woods

[57] ABSTRACT

A fungicidal composition comprising a fungicidally effective amount of
A) 1-(4-chlorophenyl)-4,4-dimethyl-3-(1,2,4-triazol-1-yl-methyl)-pentan-3-ol of the formula

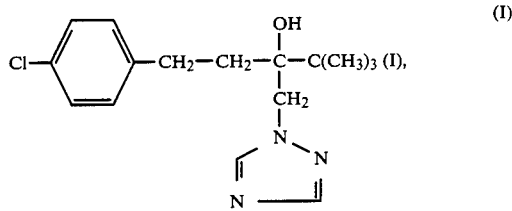

and
B) at least one member selected from the group consisting of 3-cyano-4-(2-fluoro-3-chloro-phenyl)-pyrrole of the formula

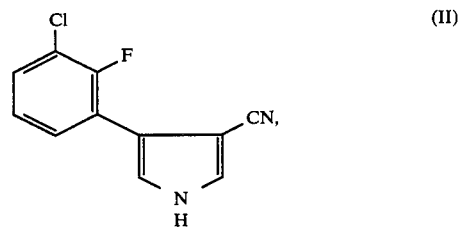

3-cyano-4-(2,4-difluoro-3-chlorophenyl)-pyrrole of the formula

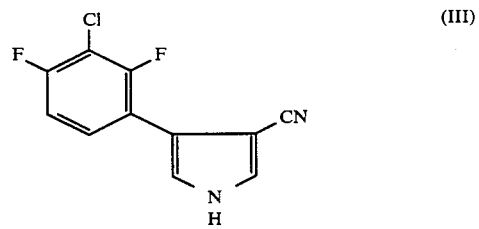

and 3-cyano-4-(2,3-dichloro-phenyl)-1-(N-methyl-N-furfuryl-aminomethyl)-pyrrole of the formula

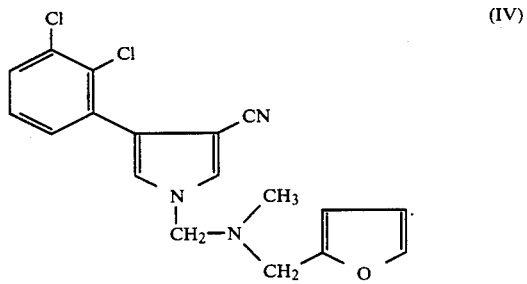

5 Claims, No Drawings

FUNGICIDAL COMBINATIONS OF ACTIVE COMPOUNDS

The present invention related to new combinations of active compounds which consist, on the one hand, of 1-(4-chlorophenyl)-4,4-dimethyl-3-(1,2,4-triazol-1-yl-methyl)-pentan-b 3-ol, which is known, and, on the other hand, of certain fungicides which are known and which are highly suitable for combating fungi.

It has already been disclosed that 1-(4-chlorophenyl)-4,4-dimethyl-b 3-(1,24,-triazol-1-yl-methyl)-pentan-3-ol has a fungicidal potency (cf. EP-OS (European Published Specification) 0,040,345). The activity of this substance is good; however, occasionally it leaves something to be desired when applied at low rates.

It is furthermore already known that 3-cyano-4-(2-fluoro-3-chloro-phenyl)-pyrrole, 3-cyano-4-(2,4-difluoro-3-chlorophenyl)-pyrrole and 3-cyano-4-(2,3-dichlorophenyl)-1-(N-methyl-N-furfurylaminomethyl)-pyrrole can be employed for combating fungi (cf. DE-OS (German Published Specification) 3,737,984 and EP-OS (European Published Specification) 0,281,731). However, the action of these substances is likewise not always satisfactory when low amounts are applied.

It has now been found that the new combinations of active compounds, consisting of A) 1-(4-chlorophenyl)-4,4-dimethyl-3-(1,2,4-triazol-1-yl-methyl)-pentan-3-ol, of the formula

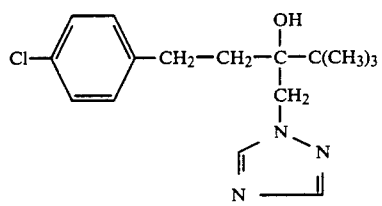

and

B) 3-cyano-4-(2-fluoro-3-chloro-phenyl)-pyrrole, of the formula

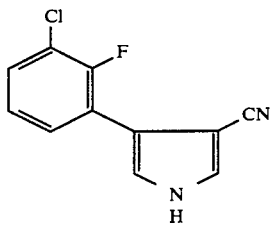

and/or 3-cyano-4-(2,4-difluoro-3-chlorophenyl)-pyrrole, of the formula

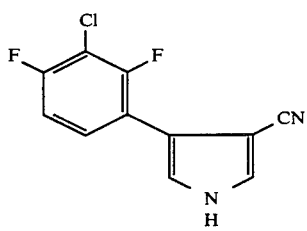

and/or 3-cyano-4-(2,3-dichloro-phenyl)-1-(N-methyl-N-furfuryl-aminomethyl)-pyrrole, of the formula

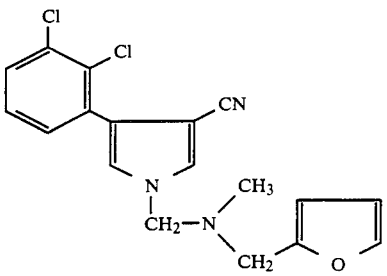

have very good fungicidal properties.

Surprisingly, the fungicidal action of the combinations of active compounds according to the invention is considerably more powerful than the total of the action of the individual active compounds. This means that true synergistic effect, which could not have been anticipated, is present and not just a supplementary action.

The active compounds contained in the combination of active compounds according to the invention are already known (cf. EP-OS (European Published Specification) 0,040,345, DE-OS (German Published Specification) 3,737,984 and EP-OS (European Published Specification) 0,281,731).

The synergistic effect is particularly pronounced when the active compounds are present in the combinations of active compounds according to the invention i specific weight ratios. However, the weight ratios c the active compounds in the combinations of activ compounds can be varied within a substantial range. I general, 0.1 to 20 parts by weight, preferably 0.2 to 1 parts by weight, of active compound of the formula (II), (III) and/or (IV) are used per part by weight b active compound of the formula (I).

The combinations of active compounds according t the invention have very good fungicidal properties an can be employed for combating phytopathogenic fung such as Plasmodiophoromycetes, Oomycetes, Chytridi omycetes, Zygomycetes, Ascomycetes, Basidiomyce tes, Deuteromycetes etc.

The combinations of active compounds according t the invention are particularly well suited for combatin; Botrytis species in viticulture, in soft fruit and in vegeta ble growing, and for combating cereal diseases, such a Fusarium, Pseudocercosporella, Rhizoctonia and Sep toria. *Fusarium nivale, Fusarium culmorum, Fusariun graminearum, Fusarium avenaceum, Pseudocercosporell. herpotrichoides, Rhizoctonia cerealis, Septoria nodorun. Septoria tritici* and *Botrytis cinerea* are mentioned a specific examples.

The good toleration, by plants, of the combinations c active compounds, at the concentrations required fo combating plant diseases, permits treatment of aeriε parts of plants, of vegetative propagation stock an seeds, and of the soil.

The combinations of active compounds according t the invention can be converted into the customary foi mulations, such as solutions, emulsions, suspension: powders, foams, pastes, granules, aerosols, very fin capsules in polymeric substances and in coating compc sitions for seed, as well as ULV formulations.

These formulations are produced in a known mannei for example by mixing the active compounds, or th combinations of active compounds, with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquid which are gaseous at ambient temperature and under atmospheric pressure, for example aerosol propellants, such as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silica, alumina and silicates. As solid carriers for granules there are rocks such as calcite, marble, pumice, sepiolite and dolomite, as well as synthetic granules or inorganic and organic meals, and granules of organic material such as sawdust, coconut shells, corn cobs and tobacco stalks. An emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations in general contain between 0.1 and 95 per cent by weight of active compound, preferably between 0.5 and 90%.

The combinations of active compounds according to the invention can be present in the formulations as a mixture with other known active compounds, such as fungicides, insecticides, acaricides and herbicides, as well as in mixtures with fertilizers and growth regulators.

The combinations of active compounds can be used as such or in the form of their formulations or the use forms prepared therefrom, such as ready-to-use solutions, emulsifiable concentrates, emulsions, suspensions, wettable powders, soluble powders and granules. They are used in the customary manner, for example by watering, spraying, atomizing, scattering, brushing on, as a dry seed treatment, a solvent-based liquid seed treatment or a liquid seed treatment, by slurry dressing or by incrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Good fungicidal action of the combinations of active compounds according to the invention can be seen from the examples which follow. While the individual active compounds have weak points in their fungicidal actions, the combinations show an action which exceeds the simple total of their actions.

A synergistic effect in fungicides is always present when the fungicidal action of the combinations of active compounds is better than the sum of the actions of the individually applied active compounds.

EXAMPLE 1

*Fusarium nivale* test (rye)/seed treatment

The active compounds are applied in the form of a dry seed dressing. They are prepared by extending the individual active compound, or the combination of active compounds, with ground minerals to give a finely pulverulent mixture which guarantees uniform distribution on the seed surface.

For the seed treatment, the infected seeds are shaken for 3 minutes together with the seed-treatment agent in a sealed glass flask.

2 batches of 100 rye grains are sown in standard soil to a depth of 1 cm, and the rye is grown in the greenhouse at a temperature of about 10° C. and a relative atmospheric humidity of about 95% in seed boxes which are exposed to light for 15 hours every day.

About 3 weeks after sowing, the plants are evaluated for symptoms of snow mould.

To demonstrate the synergism between the active compounds used in this experiment, the results were evaluated using the method described by R. S. Colby (Calculating Synergistic and Antagonistic Responses of Herbicide Combinations; Weeds 15, 20–22, 1967).

If

X denotes the degree of effectiveness, expressed in % of the untreated control, when active compound A is employed in a concentration of m mg of active compound per kg of seed, Y denotes the degree of effectiveness, expressed in % of the untreated control, when active compound B is employed in a concentration of n mg of active compound per kg of seed, and E denotes the expected degree of effectiveness, expressed in % of the untreated control, when active compounds A and B are employed in concentrations of m and n mg of active compound per kg of seed, then $$E = X + Y - \frac{X \cdot Y}{100}.$$

If the actual fungicidal action is higher than calculated, the combination is superadditive in its action, that is to say, a synergistic effect is present. In this case, the degree of effectiveness which is actually observed must be higher than the value of the expected degree of effectiveness, calculated from the abovementioned formula.

The table below shows clearly that the action which has been found, of the combinations of active compounds according to the invention, is higher than the action which has been calculated, that is to say, a synergistic effect is present.

The active compounds are applied in the form of a dry seed dressing. They are prepared by extending the individual active compound, or the combination of active compounds, with ground minerals to give a finely pulverulent mixture which guarantees uniform distribution on the seed surface.

For the seed treatment, the infected seeds are shaken for 3 minutes together with the seed-treatment agent in a sealed glass flask.

2 batches of 100 rye grains are sown in standard soil to a depth of 1 cm, and the rye is grown in the green

TABLE 1

Fusarium nivale test (rye)/seed treatment

| Active compound | Amount of active compound employed, in mg/kg of seed | Degree of effectiveness in % of the untreated control |
|---|---|---|
| Known: | | |
| 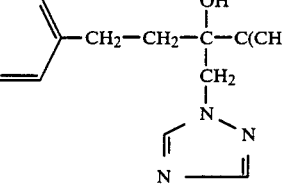 (I) | 20<br>10 | 40<br>0 |
| 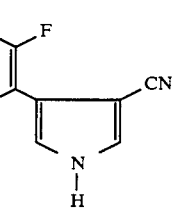 (II) | 200 | 88 |
| 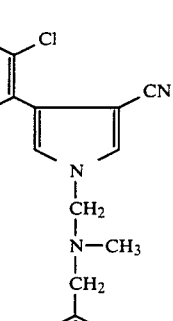 (IV) | 100 | 66 |

| According to the invention: | | Found | Calculated* |
|---|---|---|---|
| (I) + (II) (1:10) | 20 + 200 | 100 | 92.8 |
| (I) + (IV) (1:10) | 10 + 100 | 91 | 66 |
| (untreated) | — | 0 | |

*Calculated using the formula given hereinabove.

EXAMPLE 2

Fusarium nivale test (rye)/seed treatment house at a temperature of about 10° C. and a relative atmospheric humidity of about 95% in seed boxes which are exposed to light for 15 hours every day.

About 3 weeks after sowing, the plants are evaluated for symptoms of snow mold.

The active compounds, concentrations of active compounds and results of the experiments can be seen from the table below.

TABLE 2

Fusarium nivale test (rye)/seed treatment

| Active compound | Amount of active compound employed, in mg/kg of seed | Degree of effectiveness in % of the untreated control |
|---|---|---|
| Known: | | |
| 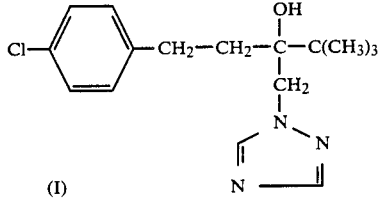 (I) | 80<br>40 | 24<br>9 |
| 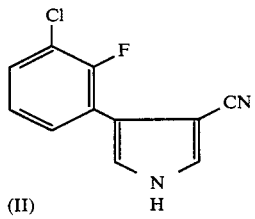 (II) | 40 | 48 |
| 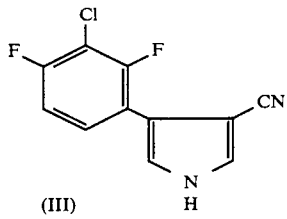 (III) | 80<br>40 | 43<br>37 |
| 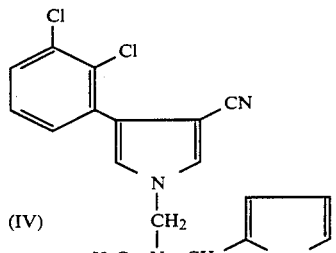 (IV) | 80 | 93 |
| untreated | — | 0 |
| According to the invention: | | |
| (I) + (II) (1:1) | 20 + 20 | 78 |
| (I) + (II) (1:7) | 5 + 35 | 93 |
| (I) + (III) (1:1) | 40 + 40 | 89 |
| (I) + (III) (1:7) | 5 + 35 | 96 |
| (I) + | 10 + | 100 |

TABLE 2-continued

Fusarium nivale test (rye)/seed treatment

| Active compound | Amount of active compound employed, in mg/kg of seed | Degree of effectiveness in % of the untreated control |
|---|---|---|
| (IV) (1:7) | | 70 |

EXAMPLE 3

Botrytis test (bean)/protective

To produce a suitable preparation of active compound, 1 part by weight of active compound, or combination of active compounds, is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the lesions on the leaves is evaluated.

To demonstrate the synergism between the active compounds used in this experiment, the results were evaluated using the method described by R. S. Colby (Calculating Synergistic and Antagonistic Responses of Herbicide Combinations; Weeds 15, 20–22, 1967).

If

X denotes the degree of effectiveness, expressed in % of the untreated control, when active compound A is employed in a concentration of m ppm Y denotes the degree of effectiveness, expressed in % of the untreated control, when active compound B is employed in a concentration of n ppm, and E denotes the expected degree of effectiveness, expressed in % of the untreated control, when active compounds A and B are employed in concentrations of m and n ppm, then $$E = X + Y - \frac{X \cdot Y}{100}.$$

If the actual fungicidal action is higher than calculated, the combination is superadditive in its action, that is to say, a synergistic effect is present. In this case, the degree of effectiveness which is actually observed must be higher than the value of the expected degree of effectiveness, calculated from the abovementioned formula.

The table below shows clearly that the action which has been found, of the combinations of active compounds according to the invention, is higher than the action which has been calculated, that is to say, a synergistic effect is present.

TABLE 3

Botrytis test (dwarf bean)/protective

| Active compound | Degree of effectiveness in % of the untreated control at an active compound concentration of | |
|---|---|---|
| | 20 ppm | 10 ppm |
| Known: | | |

TABLE 3-continued

Botrytis test (dwarf bean)/protective

| Active compound | Degree of effectiveness in % of the untreated control at an active compound concentration of | |
|---|---|---|
| | 20 ppm | 10 ppm |
| (I) [structure: Cl-phenyl-CH₂-CH₂-C(OH)(C(CH₃)₃)-CH₂-N(triazole)] | | 21 |
| (II) [structure: Cl, F-phenyl pyrrole with CN, NH] | | 10 |
| According to the invention: | | Found / Calculated* |
| (I) + (II) (2:1) | 20 ppm + 10 ppm | 72 / 29 |
| (Control) | | 0 |

*Calculated using the formula given hereinabove

EXAMPLE 4

Cochliobolus sativus test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to desired concentration.

To test for protective activity, young plants are sprayed with the preparation of active compound until dew-moist. After the spray coating has dried on, the plants are sprayed with a conidia suspension of Cochliobolus sativus.

The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after inoculation.

The active compounds, active compound concentrations and results can be seen from the following table:

TABLE 4

| | Cochliobolus sativus test (barley)/protective | |
|---|---|---|
| Active compound | Active compound concentration in the spray liquor in ppm | Degree of activity in % of the untreated control |
| known: | | |
| (I) 4-Cl-C6H4-CH2-CH2-C(OH)(C(CH3)3)-CH2-N(triazole) | 25<br>12.5 | 58<br>43 |
| (III) 3-(3-Cl-2,4-F2-phenyl)-4-cyanopyrrole | 12.5 | 0 |
| (IV) 3-(2,3-diCl-phenyl)-4-cyano-1-(N-methyl-N-furfurylamino-methyl)pyrrole | 25 | 43 |
| According to the invention: | | |
| (I) + (III) (1:1) | 6.25 + 6.25 | 58 |
| (I) + (IV) (1:1) | 12.5 + 12.5 | 72 |

EXAMPLE 5

Pyrenophora teres test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to desired concentration.

To test for protective activity, young plants are sprayed with the preparation of active compound until dew-moist. After the spray coating has dried on, the plants are sprayed with a conidia suspension of *Pyrenophora teres*.

The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

The active compounds, active compound concentrations and results can be seen from the following table.

TABLE 5

| | Pyrenophora teres test (barley)/protective | |
|---|---|---|
| Active compound | Active compound concentration in the spray liquor in ppm | Degree of activity in % of the untreated control |
| known: | | |

TABLE 5-continued

| Active compound | Pyrenophora teres test (barley)/protective | |
|---|---|---|
| | Active compound concentration in the spray liquor in ppm | Degree of activity in % of the untreated control |
| (I) 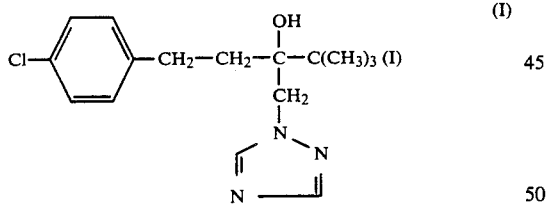 | 12.5 | 50 |
| (III) 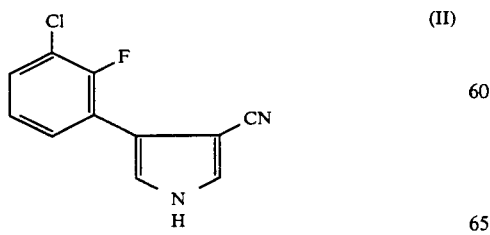 | 12.5 | 0 |
| According to the invention: | | |
| (I) + (III) (1:1) | 6.25 + 6.25 | 75 |

It will be appreciated that the instant specification is set forth by way of illustration and not limitation, and that various modifications and changes may be made without departing from the spirit and scope of the present invention.

What is claimed is:

1. A fungicidal composition comprising synergistic fungicidally effective amounts of A) 1-(4-chlorophenyl)-4,4-dimethyl-3-(1,2,4-triazol-1-yl-methyl)-pentan-3-ol of the formula

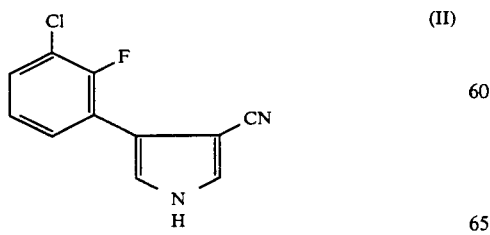

(I)

B) about 0.2 to 15 times the weight of (A) of at least one member selected from the group consisting of 3-cyano-4-(2-fluoro-3-chloro-phenyl)-pyrrole of the formula (II)

3-cyano-4-(2,4-difluoro-3-chlorophenyl)-pyrrole of the formula

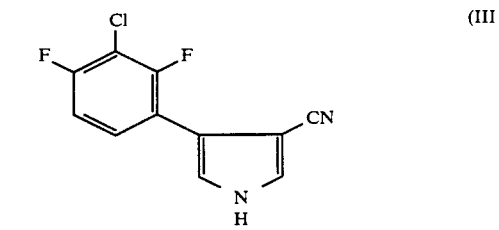

(III)

and 3-cyano-4-(2,3-dichloro-phenyl)-1-(N-methyl-N-furfuryl-aminomethyl)-pyrrole of the formula

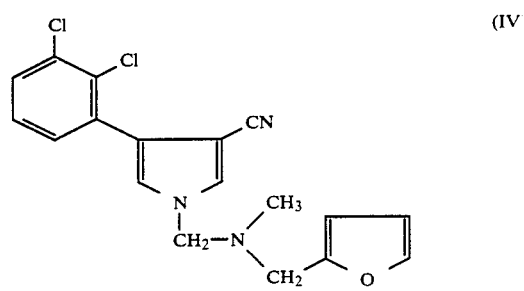

(IV)

2. A composition according to claim 1, wherein (B) is 3-cyano-4-(2-fluoro-3-chloro-phenyl)-pyrrole.

3. A composition according to claim 1, wherein (B) is 3-cyano-4-(2,4-difluoro-3-chlorophenyl)pyrrole.

4. A composition according to claim 1, wherein (B) is 3-cyano-4-(2,3-dichloro-phenyl)-1-(N-methyl-N-furfuryl-aminomethyl)-pyrrole.

5. A method of combating fungi which comprises applying to such fungi or to a locus from which it is desired to exclude such fungi a synergistic fungicidally effective amount of a composition according to claim 1.